United States Patent [19]

Bartley

[11] 4,312,955
[45] Jan. 26, 1982

[54] PROCESS FOR THE PRODUCTION OF METHANOL FROM SYNTHESIS GAS

[75] Inventor: William J. Bartley, Charleston, W. Va.

[73] Assignee: Union Carbide Corporation, New York, N.Y.

[21] Appl. No.: 211,926

[22] Filed: Dec. 1, 1980

[51] Int. Cl.$^3$ ...................... C07C 27/06; C07C 31/04
[52] U.S. Cl. .................................... 518/701; 518/713; 518/714; 518/716; 252/462
[58] Field of Search ................ 518/701, 716, 713, 714

[56] References Cited

U.S. PATENT DOCUMENTS 4,014,913  3/1977  Ellgen et al. ......................... 260/449
4,127,510  11/1978  Harrison et al. ..................... 252/462

FOREIGN PATENT DOCUMENTS 1501892  2/1978  United Kingdom .

Primary Examiner—Howard T. Mars
Attorney, Agent, or Firm—Francis M. Fazio

[57] ABSTRACT

Lanthanum rhodate, or metal substituted lanthanum rhodate, having a perovskite structure is a highly active catalyst for the production of methanol from hydrogen and carbon monoxide. The lanthanum rhodate displays excellent stability and excellent selectivity to methanol.

48 Claims, No Drawings

PROCESS FOR THE PRODUCTION OF METHANOL FROM SYNTHESIS GAS

BACKGROUND OF THE INVENTION

As the price of petroleum continues to increase and as the availability of petroleum becomes more difficult, methanol is becoming increasingly more important as a source for hydrocarbon-based fuels and chemicals. It is well known that methanol may be produced from the reaction of carbon monoxide and hydrogen. Since these two gases are readily produced from coal, which is relatively abundant, any new method for the reaction of carbon monoxide and hydrogen to form methanol would be very useful.

Catalysts of supported rhodium metal are known to hydrogenate carbon monoxide to mixtures of, predominately, acetic acid, acetaldehyde, ethanol and methane at elevated temperatures and pressures. For example, British Pat. No. 1,501,892 described a rhodium catalyzed reaction of synthesis gas so produced predominantly acetic acid and methane with some production of acetaldehyde and ethanol and U.S. Pat. No. 4,014,913 describes a synthesis gas reaction to relatively equal amounts of acetic acid, acetaldehyde and $C_1$-$C_4$ hydrocarbons with also some ethanol produced. Generally, only minor variations in this product distribution can be accomplished with catalyst additives or by manipulation of the reaction conditions.

When rhodium oxide is employed as the catalyst it is reduced in the reactor by the hydrogen and carbon monoxide reactants to rhodium metal.

DESCRIPTION OF THE INVENTION

This invention is an improved catalytic method for selectively producing methanol from hydrogen and carbon monoxide. Furthermore, any compounds which will form hydrogen and carbon monoxide, such as the mixture of water and carbon monoxide or the mixture of hydrogen and carbon dioxide, can be used as a substitute for the mixture of hydrogen and carbon monoxide used herein to exemplify the present invention.

The catalyst for the process of this invention is lanthanum rhodate, $LaRhO_3$, having a perovskite structure or lanthanum rhodate substituted with one or more other metals and also having a perovskite structure. The perovskite structure is well known to those skilled in the art. In their simplest form, perovskites have the general formula $ABO_3$, and are structurally related to the mineral $CaTiO_3$ of the same name. Ideally, their structure has a simple cubic form. The "B" ions are situated at the corners of the cube, each octahedrally coordinated to oxygen. The larger "A" ion fits into the center of the cube in the dodecahedral interstices. Perovskites are further described in such publications as F. S. Galasso, "Structure Properties and Preparation of Perovskite-Type Compounds", Pergamon, 1969 and R. J. H. Voorhoeve, "Perovskite Oxides-Materials Science in Catalysis", Science, 195, 827, 1977.

As previously indicated, the catalyst for the process of this invention is lanthanum rhodate itself, $LaRhO_3$, or a metal substituted lanthanum rhodate. By metal substituted it is meant that a portion of the rhodium and/or lanthanum ions in the perovskite structure is substituted by one or more other metal ions according to the generalized formula $$[La_{1-x}P_x][Rh_{1-y}Q_y]O_3$$

where P and Q are each one or more cations whose ionic radii, oxidation state and coordination properties are compatible with a perovskite or distorted perovskite structure. The importance of the properties of the P and Q ions to the stability of the perovskite crystal structure has been discussed by many authors, e.g. R. J. H. Voorhoeve, "Advanced Materials in Catalysis", Academic Press, N.Y., 1977, p. 129.

In the above generalized formula for the metal substituted lanthanum rhodate, Q represents one or more metal ions from the group comprising Group VIII of the Periodic Table such as iron, nickel, ruthenium, cobalt, platinum, and the like; Group IB such as copper, silver and gold; Group IIB such as zinc, cadmium and the like; Group IVB such as titanium, zirconium and the like; Group VB such as vanadium, niobium, and the like; Group VIB such as chromium, molybdenum, and the like; Group VIIB such as manganese, rhenium, and the like; and the actinides such as uranium, thorium and the like.

In the above generalized formula for the metal substituted lanthanum rhodate, P represents one or more metal ions from the group comprising Group IIA of the Periodic Table such as strontium, magnesium and the like; Group IA such as sodium, potassium and the like; Group IVA such as tin and lead; Group VA such as antimony, bismuth, and the like; the lanthanides such as cerium, neodymium and the like; and the actinides such as thorium, uranium and the like.

The ratio of the metals P and Q to lanthanum and rhodium respectively may vary widely so long as the aforementioned conditions of perovskite stability are met. In general, x and y in the generalized formula for the metal substituted lanthanum rhodate may each be from about 0.01 to about 0.99.

Lanthanum rhodate having the perovskite structure is known as are the several techniques for its preparation. A number of these known preparatory techniques are illustrated in the examples which follow. Generally, the preparatory technique involves heating a mixture of lanthanum oxide and rhodium oxide, or their precursors, in air or oxygen for sufficient times and at sufficient temperature to permit perovskite formation. Both time and temperature will vary depending on the particular composition being reacted; generally the temperature is above 800° C. and preferably it is from 950° C. to 1100° C. The lanthanum rhodate preparation can be carried out at atmospheric, subatmospheric, or superatmospheric pressure; atmospheric pressure is usually the more convenient.

The lanthanum rhodate or metal substituted lanthanum rhodate useful in the process of this invention can be employed in any form. For example, the lanthanum rhodate or metal substituted lanthanum rhodate can be employed in the form of a powder. The particle size of the powder can vary widely; generally, the smaller the particle size the higher is the catalytic activity. Preferably, the particle size is from 10 angstroms to 500 microns, most preferably from 10 angstroms to 50 microns.

Another method of employing the lanthanum rhodate or metal substituted lanthanum rhodate catalyst is as porous pellets. Such porous pellets are formed from the previously mentioned lanthanum rhodate powder using conventional pellet presses, rolling mixers, extruders or the like. Those skilled in the art of heterogeneous catalysts are familiar with the methods of preparing catalysts in porous-pellet form as well as with the beneficial additives such as dispersants, binders, lubricants and the like which are useful in such preparation.

Still another method of employing the lanthanum rhodate or metal substituted lanthanum rhodate catalyst useful in the process of this invention is as a dispersion in a suitable solvent. Such a solvent must be sufficiently inert so as to not substantially degrade or otherwise interfere with the synthesis of hydrogen and carbon monoxide to methanol.

Illustrative of such sutiable solvents one can name methylcyclohexane, nonane, dioxane, tetrahydrofuran, methanol, ethanol, propanol, butanol, butyrolactone, methylacetate, ethyl acetate, mono-and dialkyl ethylene glycol ethers, mono-and dialkyl propylene glycol ethers, and the like. The preferred solvent for this application is dioxane. When employed as a dispersion in a solvent the rhodate catalyst is present in a concentration in the solvent of from 0.01 to 50 weight percent, preferably from 0.1 to 15 weight percent, based on the weight of the solvent.

Still another method of employing the lanthanum rhodate or metal substituted lanthanum rhodate catalyst of the process of this invention is on a support. Illustrative of such suitable supports one can name silicon dioxide, aluminum oxide, magnesium oxide, titanium dioxide, magnesium aluminate, zirconium dioxide, silicon carbide, ceramic, diatomaceous earth, pumice and many others known to those skilled in the art.

As is known, the support must be sufficiently inert so as to not unduly interfere with the formation of methanol from the reaction of hydrogen and carbon monoxide. When present in this form the lanthanum rhodate or metal substituted lanthanum rhodate is present in a concentration of from 0.01 to 50 weight percent, preferably from 0.1 to 20 weight percent, based on the weight of the support.

The preparation of a catalyst on a support is well known; nevertheless, two methods for illustrative purposes will be mentioned. For example, one can disperse the powdered lanthanum rhodate or metal substituted lanthanum rhodate through a support having pores of sufficient diameter to allow incorporation of the catalyst particles onto the support; a convenient method of accomplishing this is by suspending the powdered catalyst in a suitable solvent such as water, methanol, ethanol, acetone, or other organic liquid of appropriate viscosity and boiling point, impregnating the support with this mixture using standard techniques well known to those skilled in the art and then evaporating the solvent. An alternative technique for preparing a catalyst on a support is to apply a solution of lanthanum rhodate perovskite precursors, such as lanthanum nitrate and rhodium nitrate, to a sufficiently non-reactive and high melting support, such as $SiO_2$ or $MgAl_2O_4$, followed by drying and firing at temperatures and for times sufficient for perovskite formation. Those skilled in the art are familiar with many other methods to prepare catalysts coated on supports as well as other methods to employ a catalyst for the reaction of hydrogen and carbon monoxide.

The lanthanum rhodate or metal substituted lanthanum rhodate, perovskite catalyst is present in the reaction mixture in any catalytically effective amount sufficient to catalyze the reaction of hydrogen and carbon monoxide to methanol. When operating in the slurry, or batch mode, the mole ratio of catalyst to carbon monoxide is preferably from about $10^{-4}$ to about $10^{-1}$, most preferably from about $10^{-3}$ to $10^{-2}$. Under continuous vapor-phase conditions, the hourly space velocity, i.e. the volume of reactant gas at 0° C. and 760 mm Hg pressure per volume of catalyst per hour, is preferably in excess of $10^2$, most preferably from $10^3$ to $10^5$. Excessively high space velocities generally result in uneconomically low conversions and excessively low space velocities often result in lower methanol efficiencies.

In the reaction mixture the mole ratio of hydrogen to carbon monoxide may be from 20:1 to 1:20; preferably from about 5:1 to about 1:5; most preferably from 2:1 to 1:2. Generally, the activity of the catalyst is increased with an increase in this mole ratio and selectivity to methanol is generally not adversely affected by small increases in the mole ratio though a a large increase in the hydrogen to carbon monoxide mole ratio may reduce somewhat the selectivity of the reaction to methanol.

The pressure of the reaction can be from 100 psig to 15000 psig, preferably from 1000 psig to 5000 psig. Generally, both the activity and the selectivity of the catalyst to methanol increase as the pressure increases though it is well known that increases in operating pressure are generally associated with increases in costs.

The temperature of the reaction can be from 150° C. to 450° C., preferably from 200° C. to 400° C., most preferably from 250° C. to 300° C. Generally, the greater the reaction temperature the greater is the catalyst activity but there is generally observed a concomitant decrease in catalyst selectivity to methanol as reaction temperature is increased.

The time of the reaction will vary and is somewhat dependent on the reaction parameters employed and the individual reactants employed.

The lanthanum rhodate perovskite catalyst is unexpectedly very stable over time and evidences very little if any reduction to bulk metal along with the associated detrimental effects upon catalyst activity. In fact, there is often observed an increase in the activity of the catalyst over time. Such a finding is very surprising and unexpected. Although not wishing to be tied down to any theory, applicant offers as one explanation for this surprising phenomenon that partial or complete removal of the perovskite surface oxide occurs under reaction conditions thus creating the catalytic sites believed necessary for the hydrogenation of carbon monoxide to methanol. Another explanation is that oxygen vacancies are created within the perovskite matrix during in situ reduction; the oxygen vacancies may be important to the catalysis.

The process of this invention can be carried out continuously or in batch. In a typical laboratory scale batch process, the catalyst is charged to the reactor with a suitable solvent, the reactor is purged then charged with hydrogen and carbon monoxide in the desired mole ratio to the desired pressure; the reactor is sealed, and heated at the desired temperature for a specified time.

The process of this invention provides a novel and highly efficient method for producing methanol from the relatively inexpensive and abundant reactants, hydrogen and carbon monoxide. This novel process described herein is of considerable economic and strategic importance. Given the importance of producing hydrocarbons from synthetic processes any novel and efficient method to produce methanol is highly desirable.

It was completely unexpected that the lanthanum rhodate, or metal substituted lanthanum rhodate, perovskite catalyst useful in this invention would exhibit such stability under catalytic conditions and would also convert hydrogen and carbon monoxide to methanol at such high activity and selectivity.

The following examples serve to further illustrate the process of this invention; they are not intended to limit the invention in any way.

EXAMPLE 1

Catalyst Preparation

An equimolar mixture of rhodium trichloride, $RhCl_3 \cdot xH_2O$, and lanthanum nitrate, $La(NO_3)_3 \cdot 6H_2O$, in a minimum of distilled water was evaporated to dryness by gentle warming on a hot plate. The dry powder was ground thoroughly and then transferred to a quartz boat. The mixture was fired in air in a muffle furnace at 950°–1000° C. for 18–24 hours, after which the product was cooled on the bench top.

The product thus obtained was lanthanum rhodate having a perovskite structure as confirmed by X-ray diffration analysis.

The finished perovskite was ground with a mortar and pestle until it would pass a 325-mesh screen; this corresponded to a particle size of about 45 microns. A slurry of 3 grams of the finely pulverized perovskite was suspended in 16 ml of distilled water, and the mixture was added rapidly and with good agitation to 27 grams of oxalic acid-washed, 8–20 mesh, alpha-aluminum oxide (Norton SA-5105 "MACROPORT"). The impregnated support was dried slowly under nitrogen by heating in an oven for one hour at 85° C., then for five hours at 120° C. The finished supported catalyst contained 10 weight percent lanthanum rhodate. Visual inspection of fractured catalyst particles showed the perovskite was evenly distributed throughout.

METHANOL SYNTHESIS

The reactor employed was a 316-stainless steel, bottom-agitated "Magnedrive" autoclave of the J. M. Berty design with a centrally positioned catalyst basket and a side product effluent line. A variable speed, magnetically driven fan continuously recirculated the reaction mixture over the catalyst bed. Hydrogen feed gas was introduced continuously through a separate port at the bottom of the autoclave in order to avoid a hydrogen-rich zone in the autoclave. Effluent gases were removed through a port in the side of the reactor. Condensable liquid products were removed from the exit stream in a brine-cooled condenser at about 5° to 10° C. and were collected in a holding tank under pressure. The non-condensable components of the exit stream were vented through a wet-test meter at atmospheric pressure to determine their total volume. A rubber septum in the atmospheric pressure line permitted syringe sampling of the non-condensable gases. No external recycle was employed.

The catalyst basket was charged with 20 grams of the supported catalyst prepared above. Gold-plated screens and thin layers of glass wool were placed above and below the catalyst bed to prevent circulation of solid fines. The catalyst basket was placed in the reactor and the reactor then sealed. The sealed reactor and the process lines were pressure tested at ambient temperatures to a pressure of 2500 psig with hydrogen. When the reactor was shown to be leak free, helium was used to purge the system and to pressurize the reactor to 2500 psig. The catalyst was heated to 200° C. under static helium pressure and the hydrogen and carbon monoxide flows were started. The flow rates were adjusted to give a 1:1 $H_2/CO$ mole ratio and an approximate purge rate of 500 STP (standard temperature and pressure, 0° C. and 1 atmosphere) liters per hour. This corresponds to a space velocity of about 25,000 STP volumes of gas per volume of catalyst per hour. The hydrogen:carbon monoxide mole ratio was determined by gas chromatographic analysis of an effluent gas aliquot.

When the appropriate gas composition was obtained, the reactor temperature was raised to 250° C. A period from about 0.5 hour to about 1 hour was allowed for the reactor to reach a steady-state at the new temperature. The liquid product trap was then drained, a wet-test meter reading was taken, and the time was noted as the beginning of a run.

The product gas was analyzed for hydrogen, carbon monoxide, methane, methanol, ethanol and acetaldehyde using gas chromatographic analysis. Liquid samples were analyzed on a 10 foot by $\frac{1}{8}$ inch Poropak PS column by programming from 70°–185° C. at 5° C./minute. The helium carrier flow was 30 ml/minute, and the detector and injector temperatures were 240° C. and 245° C., respectively.

Succeeding runs with the same catalyst were made either at the same conditions or at new conditions of temperature and/or pressure. If any of the conditions were changed, approximately one hour was allowed for the reaction to come to a new steady-state before beginning a new run.

Thirty-three runs were made, each using the same 20 grams of supported catalyst charged. The process conditions for each run are shown in Table I along with the results. In Table I the time represents the cumulative running time of the runs, the indicated time being the end of that particular run, and the difference between any two being the time period of that particular run. The rates shown are calculated on the basis of lanthanum rhodate weight. Efficiencies shown represent the moles of carbon in a given product taken as a percentage of the total moles of carbon in all the recovered products. The products listed as others are ethanol and acetaldehyde; ND indicates not detected; MeOH indicates methanol and $CH_4$ indicates methane.

TABLE I

| Run No. | Time (hrs) | Temp (°C.) | $H_2$:CO Mole Ratio | Pressure (psig) | Rate (mole/Kg $LaRhO_3$/hr.) | | | Efficiency (%) | | |
|---|---|---|---|---|---|---|---|---|---|---|
| | | | | | MeOH | $CH_4$ | OTHERS | MeOH | $CH_4$ | OTHERS |
| 1 | 4.5 | 250 | 1:1 | 2500 | 12.9 | 0.8 | ND | 94 | 6 | — |
| 2 | 6.5 | 250 | 1:1 | 2500 | 15.5 | 0.3 | ND | 98 | 2 | — |
| 3 | 15(a) | 250 | 1:1 | 2500 | 26 | 0.3 | 0.25 | 96 | 1 | 2.4 |
| 4 | 25 | 250 | 1:1 | 2500 | 29 | 1 | 0.24 | 95 | 3 | 1.3 |
| 5 | 27 | 250 | 1:1 | 2500 | 30.9 | ND | 0.25 | 98 | — | 1.3 |
| 6 | 29 | 250 | 1:1 | 2500 | 29.2 | 0.3 | 0.13 | 98 | 1 | 1 |

TABLE I-continued

| Run No. | Time (hrs) | Temp (°C.) | H$_2$:CO Mole Ratio | Pressure (psig) | Rate (mole/Kg LaRhO$_3$/hr.) | | | Efficiency (%) | | |
|---|---|---|---|---|---|---|---|---|---|---|
| | | | | | MeOH | CH$_4$ | OTHERS | MeOH | CH$_4$ | OTHERS |
| 7 | 38[a] | 250 | 1:1 | 2500 | 33.3 | 0.2 | 0.12 | 99 | <1 | 0.6 |
| 8 | 49 | 250 | 1:1 | 2500 | 31.8 | 0.5 | 0.01 | 99 | 1 | .1 |
| 9 | 51 | 250 | 1:1 | 2500 | 24.7 | ND | ND | 100 | — | — |
| 10 | 53 | 250 | 1:1 | 2500 | 25.1 | ND | 0.04 | 100 | — | 0.4 |
| 11 | 58 | 250 | 1:1 | 2500 | 29.1 | 0.9 | 0.13 | 95 | 3 | 1.2 |
| 12 | 66[a] | 250 | 1:1 | 2500 | 30.5 | 0.7 | 0.13 | 97 | 2 | 1.2 |
| 13 | 76 | 250 | 1:1 | 2500 | 29 | 1 | 0.13 | 95 | 3 | 1.2 |
| 14 | 78 | 250 | 1:1 | 1000 | 13.5 | ND | ND | 100 | — | — |
| 15 | 81 | 250 | 1:1 | 1000 | 12.4 | 0.2 | ND | 98 | 2 | — |
| 16 | 82 | 250 | 1:1 | 1000 | 12.1 | 0.2 | ND | 98 | 2 | — |
| 17 | 90[a] | 250 | 1:1 | 1000 | 13.3 | 0.5 | ND | 97 | 3 | — |
| 18 | 102 | 250 | 2:1 | 1000 | 17.6 | 0.5 | ND | 97 | 3 | — |
| 19 | 104 | 250 | 2:1 | 1000 | 19.5 | 0.7 | ND | 97 | 4 | — |
| 20 | 106 | 250 | 2:1 | 1000 | 17.4 | 0.7 | ND | 96 | 4 | — |
| 21 | 114[a] | 250 | 1.6:1 | 2500 | 32.4 | 1.1 | 0.12 | 96 | 3 | 0.7 |
| 22 | 124 | 250 | 1.6:1 | 2500 | 35.4 | 1 | 0.12 | 96 | 3 | 0.7 |
| 23 | 126 | 250 | 1.6:1 | 2500 | 40.5 | 1.4 | 0.1 | 96 | 3 | 0.5 |
| 24 | 129 | 250 | 1:1 | 2500 | 27 | 1.4 | ND | 95 | 5 | — |
| 25 | 130 | 250 | 1:1 | 2500 | 28.1 | 0.8 | ND | 97 | 3 | — |
| 26 | 139[a] | 250 | 1:1 | 2500 | 35.3 | 1.7 | 0.07 | 95 | 5 | 0.4 |
| 27 | 147 | 250 | 1:1 | 2500 | 32 | 1.5 | ND | 96 | 4 | — |
| 28 | 152 | 275 | 1:1 | 2500 | 60.8 | 5.6 | 0.8 | 89 | 8 | 2.3 |
| 29 | 154 | 275 | 1:1 | 2500 | 65.7 | 4.4 | 1 | 91 | 6 | 2.4 |
| 30 | 158[b] | 250 | 1:1 | 2500 | 23 | 1 | 0.14 | 95 | 4 | 1.1 |
| 31 | 159 | 250 | 1:1 | 2500 | 31 | 0.8 | 0.12 | 97 | 3 | 0.7 |
| 32 | 167[a] | 250 | 1:1 | 2500 | 28.1 | 0.8 | 0.09 | 96 | 3 | 0.6 |
| 33 | 177 | 250 | 1:1 | 2500 | 30.4 | 0.6 | 0.06 | 98 | 2 | 0.4 |

[a]Overnight run. Products were collected in one 16 to 18 hour sample, and are reported against the averaged time.
[b]Following weekend shut down.

DISCUSSION OF RESULTS

The results demonstrate the excellent catalytic ability of lanthanum rhodate for the conversion of hydrogen and carbon monoxide to methanol. The catalyst displays excellent activity, selectivity and stability.

Comparison of run 14-17 at 1000 psig with runs 1-13, 24-27 and 30-33 at 2500 psig, wherein in all these runs the H$_2$:CO molar ratio was 1:1 and the temperature was 250° C., shows that the catalyst activity, reported as rate, is generally greater at the higher pressure and that the selectivity, reported as efficiency, is not significantly detrimentally affected.

Comparison of runs 14-17 at H$_2$:CO of 1:1 with runs 18-20 at H$_2$:CO of 2:1, wherein in all these runs the total pressure is 1000 psig and the temperature is 250° C., shows that the catalyst activity is generally greater at the higher hydrogen partial pressure while the selectivity is not significantly adversely affected.

Comparison of runs 1-13, 24-27 and 30-33 at 250° C. with runs 28-29 at 275° C., wherein in all these runs the total pressure is 2500 psig and the H$_2$:CO mole ratio is 1:1, shows that catalyst activity is greater at the higher temperature though the selectivity of the catalyst is reduced from about 98 percent to about 90 percent selectivity to methanol.

Comparison of run 1-13 at an average cumulative reaction time of 38 hours with runs 24-27 at an average cumulative reaction time of 138 hours and with runs 30-33 at an average cumulative reaction time of 168 hours, wherein in all these runs the total pressure was 2500 psig, the H$_2$:CO mole ratio was 1:1 and the reaction temperature was 250° C., shows the excellent stability of the catalyst. Neither the activity nor the selectivity show a decline over the time period of the entire set of runs, dramatically demonstrating the excellent stability of the lanthanum rhodate catalyst; this is in contrast to the well known instability of rhodium oxide to in situ reduction to the metal, giving catalysts with little or no methanol activity.

EXAMPLE 2

Lanthanum rhodate having a perovskite structure was prepared in a manner similar to that of Example 1 and was ground with a mortar and pestle until it would pass a 200-mesh screen; this corresponded to a particle size of about 75 micron. A mixture was prepared by admixing 0.5 gram of the pulverized perovskite with 50 ml of dioxane and about 0.5 gram of nonane (internal standard for g.l.c. analysis). The mixture was charged to a 316-stainless steel, 300-ml, magnetically stirred batch reactor equipped with individual hydrogen and carbon monoxide inlet lines for pressurization and a separate vent line for discharging products. This autoclave was purged two times with 500 psig of hydrogen, pressure tested with hydrogen at 3500 psig, vented to atmospheric pressure, then charged with 1800 psig of hydrogen and carbon monoxide in a mole ratio of 1.06:1. The agitator was started and adjusted to 1000 rpm and the temperature of the reactor contents was brought to 250° C. The reaction was carried out at a pressure of from about 3100 to 3500 psig.

After six hours of the reaction the autoclave was cooled, agitation was discontinued and the pressure was vented slowly through a wet-test meter. During this venting process a sample of product gas was collected through a tee located in the vent line between the reactor and the wet-test meter. The product gas and liquid were analyzed using a procedure similar to that employed in Example 1. The rate to methanol reported as moles/kg. LaRhO$_3$/hr. was 3.3 and the rate to other products was 0.56. Other products included methyl formate, propionaldehyde, methyl acetate, n-propanol, acetic acid, n-butanol, ethylene and methane. The selectivity to methanol, measured as efficiency as defined in Example 1, was 75 percent.

The procedure described above was repeated for another six hours using the same catalyst. The $H_2:CO$ mole ratio was 1.09:1. Analysis of the product gas showed a rate to methanol of 9.45 moles/kg. $LaRhO_3$/hr., a rate to other products of 1.03 moles/kg. $LaRhO_3$/hr., and a selectivity to methanol of 85 percent.

EXAMPLE 3

The procedure described in Example 2 was repeated except that 50 ml of tetrahydrofuran was substituted for the 50 ml of dioxane used in Example 2 and the $H_2:CO$ mole ratio was 1.05:1. An analysis of the products similar to that described in Example 2 showed a rate to methanol of 0.79, a rate to ethanol of 0.09 and a rate to hydrocarbons of 0.38 signifying a selectivity to methanol of 35 percent.

The procedure was repeated using the same catalyst. The $H_2:CO$ mole ratio was 1.03:1. Analysis of the product gas showed a rate to methanol of 3.42 moles/kg. $LaRhO_3$/hr., a rate to ethanol of 0.06 and a rate to hydrocarbons of 0.37; the selectivity to methanol was 76 percent.

EXAMPLE 4

An equimolar mixture of $RhCl_3 \cdot xH_2O$ and $La(NO_3)_3 \cdot 6H_2O$ was ground together in a mortar until intimately mixed. The powder was transferred to a quartz boat, and placed in an air-swept furnace which had been preheated to 650° C. The temperature was increased to 1000° C. and was held there for 20 hours. The product was cooled on the bench top, reground and then returned to the 1000° C. furnace for an additional 22 hours. The product thus obtained was lanthanum rhodate having a perovskite structure; the structure was confirmed by X-ray diffraction analysis.

Thereafter the procedure of Example 2 was employed except that the $H_2:CO$ mole ratio was 1.29:1. An analysis of the products similar to that described in Example 2 showed a rate to methanol of 1.6, a rate to ethanol of 0.04 and a rate to hydrocarbons of 0.35 signifying a selectivity to methanol of 77 percent.

EXAMPLE 5

Sufficient $La(NO_3)_3 \cdot 6H_2O$ was dissolved in a 10 weight percent aqueous solution of $RhCl_3 \cdot xH_2O$ to give an equimolar mixture. The well-stirred solution was precipitated with a slight excess of 6 N ammonium hydroxide and stirred overnight at room temperature. The precipitate was allowed to settle and was then filtered by suction. After drying at 110° C. for 24 hours, the material was transferred to a quartz dish and was fired in air in a muffle furnace for 18 hours at 1000° C. The product was cooled on the bench top, reground, and then returned to the 1000° C. furnace for an additional 20 hours. The product thus obtained was lanthanum rhodate having a perovskite structure; the structure was confirmed by X-ray diffraction analysis.

Thereafter the procedure of Example 2 was employed except that the $H_2:CO$ mole ratio was 0.37:1. An analysis of the products similar to that described in Example 2 showed a rate to methanol of 0.78, a rate to ethanol of 0.07 and a rate to hydrocarbons of 0.27, signifying a selectivity to methanol of 54 percent.

EXAMPLE 6

Lanthanum rhodate having a perovskite structure was prepared in a manner similar to that of Example 1 except that after the mixture was fired in air in a muffle furnace at 1000° C. for 19 hours the mixture was cooled to about 200° C. in the furnace over a 2 hour period; then, as in Example 1, the quartz boat was transferred to the bench top and allowed to cool to room temperature.

Thereafter the procedure of Example 2 was employed except that the $H_2:CO$ mole ratio was 1.04:1. An analysis of the products similar to that described in Example 2 showed a rate to methanol of 2.6, a rate to ethanol of 0.14 and a rate to hydrocarbons of 0.97, signifying a selectivity to methanol of 57 percent.

EXAMPLE 7

Lanthanum rhodate having a perovskite structure was prepared in a manner similar to that of Example 1. Thereafter the procedure of Example 2 was employed for seven runs with the same initial catalyst charge which amounted to 0.56 gram of $LaRhO_3$. Each of the runs was carried out at 250° C. but each employed at different $H_2:CO$ mole ratio as shown in Table II. The time shown in Table II is the cumulative time at the time of product analysis. The products were analyzed as described in Example 2 and the results are reported in Table II. MeOH indicates methanol and HC indicates methane, ethane and/or ethylene.

TABLE II

| Run No. | Time (hrs.) | $H_2:CO$ Mole Ratio | Rate (mole/kg $LaRhO_3$/hr) | | Efficiency (%) | |
|---|---|---|---|---|---|---|
| | | | MeOH | HC | MeOH | HC |
| 1 | 6 | 0.64 | 0.84 | 0.71 | 41 | 37 |
| 2 | 12 | 0.76 | 3.3 | 1 | 64 | 16 |
| 3 | 18 | 1.41 | 4.5 | 1 | 72 | 17 |
| 4 | 24 | 0.93 | 7.9 | 0.86 | 79 | 9 |
| 5 | 30(a) | 1.35 | 8 | 0.63 | 87 | 7 |
| 6 | 38 | 2.71 | 15 | 1.2 | 87 | 7 |
| 7 | 42 | 2.50 | 24.8 | 1.1 | 88 | 4 |

(a)Catalyst was isolated just prior to this run and was recharged with fresh solvent.

The results further demonstrate that the lanthanum rhodate is a highly stable catalyst which evidences increased activity and selectivity with time in the production of methanol from hydrogen and carbon monoxide.

EXAMPLE 8

A number of runs were carried out using the equipment and a procedure similar to that described in Example 1 except that metal substituted lanthanum rhodate was employed. Each metal substituted lanthanum rhodate catalyst was prepared following a procedure similar to that described in Example 1 for the preparation of lanthanum rhodate except that there was also added to the mixture of rhodium trichloride and lanthanum nitrate a stoichiometric amount of a metal oxide, metal halide or metal oxide precursor containing the metal to be substituted. By stoichiometric amount it is meant that amount which would result in the formula listed in Table III. As in Example 1, the mixture was ground to a fine powder, transferred to a quartz boat and fired in air in a muffle furnace to obtain the metal substituted lanthanum rhodate having a perovskite structure.

Each run was carried out at 250° C., 3500 psig, employing from about 0.5 to about 1 gram of catalyst, and with 50 grams of dioxane as solvent. The other test parameters varied for each run and these parameters are reported in Table III along with the particular metal substituted lanthanum rhodate employed. Some of the catalyst runs were repeated and this is indicated by the reaction time which is reported as the cumulative time for each particular catalyst charge. Each individual run lasted six hours.

The products were analyzed as in Example 1 and the results are shown in Table III. In the table the following abbreviations are used: Oxygenated products-$C_1$=methanol, $C_2$=ethanol and/or acetaldehyde, $C_3$=propanol and/or propionaldehyde, $C_4$-butanols, butyraldehyde and/or crotonaldehyde; Hydrocarbons-$C_1$=methane, $C_2$=ethane and/or ethylene, $C_3$=propanes and/or propene, $C_4$=butanes and/or butenes.

The results demonstrate that metal substituted lanthanum rhodates are effective selective catalysts for the production of methanol from the reaction of hydrogen and carbon monoxide.

TABLE III

| Catalyst | Time (hrs) | $H_2$:CO (mole ratio) | Total Rate (mole/kg cat./hr.) | Oxygenated Products $C_1$ | $C_2$ | $C_3$ | $C_4$ | Hydrocarbons $C_1$ | $C_2$ | $C_3$ | $C_4$ |
|---|---|---|---|---|---|---|---|---|---|---|---|
| $La_{0.8}Sr_{0.2}RhO_3$ | 6 | 0.94 | 3.2 | 49 | 6 | — | — | 34 | 5 | 2 | — |
| $La_{0.8}Sr_{0.2}RhO_3$ | 12 | 0.98 | 6.2 | 63 | 9 | 2 | 3 | 18 | 3 | 1 | — |
| $La_{0.96}Th_{0.04}RhO_3$ | 6 | 1.3 | 6.7 | 63 | 7 | 1 | — | 23 | 2 | 9 | — |
| $La(Zn_{0.5}Rh_{0.5})O_3$ | 6 | 1.11 | 0.23 | 58 | 7 | — | — | 33 | — | — | — |
| $La(Zn_{0.5}Rh_{0.5})O_3$ | 12 | 2.06 | 1.8 | 80 | 1 | 5 | — | 13 | 1 | — | — |
| $La(Cu_{0.5}Rh_{0.5})O_3$ | 6 | 1.9 | 6.2 | 47 | 6 | 21 | — | 22 | 2 | 1 | — |
| $La(Pt_{0.1}Rh_{0.9})O_3$ | 6 | 1.01 | 2.2 | 75 | 5 | — | — | 15 | 1 | — | — |
| $La(Pt_{0.1}Rh_{0.9})O_3$ | 12 | 0.98 | 7.7 | 78 | 4 | 1 | 2 | 9 | 1 | — | — |
| $La(U_{0.33}Rh_{0.67})O_3$ | 6 | 2.38 | 2.3 | 46 | 6 | 23 | 3 | 17 | 4 | 1 | — |
| $La(U_{0.33}Rh_{0.67})O_3$ | 12 | 2.32 | 2.0 | 60 | 5 | 5 | — | 22 | 5 | 1 | — |
| $La(Cu_{0.45}Cr_{0.45}Rh_{0.1})O_3$ | 6 | 2.16 | 0.67 | 79 | — | — | — | 21 | — | — | — |
| $La(Cu_{0.25}Cr_{0.25}Rh_{0.5})O_3$ | 6 | 1.84 | 1.5 | 43 | 15 | 3 | 6 | 31 | 3 | — | — |
| $La(Cu_{0.25}Cr_{0.25}Rh_{0.5})O_3$ | 12 | 1.98 | 2.7 | 72 | 8 | — | 2 | 15 | 1 | — | — |
| $La(Cu_{0.25}Cr_{0.25}Rh_{0.5})O_3$ | 18 | 2.14 | 4.9 | 70 | 5 | 2 | — | 17 | 1 | — | — |
| $La(Cu_{0.05}Cr_{0.05}Rh_{0.9})O_3$ | 6 | 2.07 | 3.2 | 51 | 9 | 3 | — | 26 | 6 | 4 | 1 |
| $La(Cu_{0.05}Cr_{0.05}Rh_{0.9})O_3$ | 12 | 1.95 | 6.8 | 72 | 3 | 3 | 3 | 9 | 1 | 1 | — |
| $La(Cu_{0.25}Fe_{0.25}Rh_{0.5})O_3$ | 6 | 1.98 | 3.2 | 55 | 12 | 7 | 4 | 16 | 5 | 1 | — |
| $La(Cu_{0.25}Fe_{0.25}Rh_{0.5})O_3$ | 12 | 1.98 | 3.0 | 71 | 4 | 8 | — | 14 | 1 | — | — |
| $La(Cu_{0.25}V_{0.25}Rh_{0.5})O_3$ | 6 | 2.06 | 3.5 | 67 | 4 | 12 | 2 | 15 | 1 | — | — |
| $La(Cu_{0.25}Ti_{0.25}Rh_{0.5})O_3$ | 6 | 1.98 | 4.9 | 38 | 12 | 1 | 3 | 41 | 3 | 2 | — |
| $La(Cu_{0.25}Ti_{0.25}Rh_{0.5})O_3$ | 12 | 2.27 | 4.7 | 58 | 18 | 4 | — | 25 | 1 | — | — |
| $La(Ni_{0.5}Rh_{0.5})O_3$ | 6 | 1.98 | 1.5 | 61 | — | — | — | 33 | 3 | 1 | — |
| $La(Ni_{0.5}Rh_{0.5})O_3$ | 12 | 2.05 | 4.6 | 82 | 1 | 1 | — | 13 | 1 | — | — |
| $La(Ni_{0.5}Rh_{0.5})O_3$ | 6 | 1.01 | 0.53 | 49 | — | — | — | 51 | — | — | — |
| $La(Ni_{0.5}Rh_{0.5})O_3$ | 12 | 1.11 | 1.7 | 60 | 8 | 4 | — | 22 | 1 | — | — |
| $La(Ni_{0.5}Rh_{0.5})O_3$ | 18 | 1.0 | 2.3 | 70 | 6 | — | — | 17 | 1 | — | — |
| $La(Co_{0.2}Rh_{0.8})O_3$ | 6 | 1.26 | 2.89 | 50 | 10 | — | 2 | 31 | 3 | 2 | — |
| $La(Co_{0.2}Rh_{0.8})O_3$ | 12 | 1.12 | 7.8 | 48 | 10 | 11 | 2 | 15 | 1 | 1 | 3 |

What is claimed is:

1. A process for the selective production of methanol comprising contacting a mixture of hydrogen and carbon monoxide with a catalytic amount, sufficient to catalyze the reaction, of lanthanum rhodate having a perovskite structure, wherein the hydrogen to carbon monoxide mole ratio is from 20:1 to 1:20 and the reaction is carried out at a pressure of from 100 psig to 15000 psig and a temperature of from 150° C. to 450° C.

2. A process as claimed in claim 1 wherein said process is carried out in batch in a slurry.

3. A process as claimed in claim 2 wherein the lanthanum rhodate catalyst is present in a concentration of from $10^{-4}$ to $10^{-1}$ mole per mole of carbon monoxide.

4. A process as claimed in claim 2 wherein the lanthanum rhodate catalyst is present in a concentration of from $10^{-3}$ to $10^{-2}$ mole per mole of carbon monoxide.

5. A process as claimed in claim 1 wherein said process is carried out continuously in the vapor phase.

6. A process as claimed in claim 5 wherein the volume of reactant gas, at standard conditions of 0° C. and 760 mm Hg, per volume of catalyst exceeds $10^2$.

7. A process as claimed in claim 5 wherein the volume of reactant gas, at standard conditions of 0° C. and 760 mm Hg, per volume of catalyst is from $10^3$ to $10^5$.

8. A process as claimed in claim 1 wherein said lanthanum rhodate is present in the form of a powder having a particle size of from 0.001 to 500 microns.

9. A process as claimed in claim 8 wherein said particle size is from 0.001 to 50 microns.

10. A process as claimed in claim 1 wherein said lanthanum rhodate is present in the form of porous pellets.

11. A process as claimed in claim 1 wherein said lanthanum rhodate is present in the form of a dispersion in a substantially inert solvent.

12. A process as claimed in claim 11 wherein the lanthanum rhodate is present in said dispersion in a concentration of from 0.01 to 50 weight percent based on the weight of said solvent.

13. A process as claimed in claim 12 wherein said concentration is from 0.1 to 15 weight percent.

14. A process as claimed in claim 11 wherein said substantially inert solvent is dioxane.

15. A process as claimed in claim 11 wherein said substantially inert solvent is tetrahydrofuran.

16. A process as claimed in claim 1 wherein said lanthanum rhodate is present in the form of a coating on a support.

17. A process as claimed in claim 16 wherein said lanthanum rhodate is present in a concentration of from 0.01 to 50 weight percent based on the weight of the support.

18. A process as claimed in claim 16 wherein said concentration is from 0.1 to 20 weight percent.

19. A process as claimed in claim 16 wherein said support is aluminum oxide.

20. A process as claimed in claim 1 wherein said hydrogen to carbon monoxide mole ratio is from 5:1 to 1:5.

21. A process as claimed in claim 1 wherein said hydrogen to carbon monoxide mole ratio is from 2:1 to 1:2.

22. A process as claimed in claim 1 wherein said pressure is from 1000 psig to 5000 psig.

23. A process as claimed in claim 1 wherein said pressure is from 1000 psig to 2500 psig.

24. A process as claimed in claim 1 wherein said temperature is from 200° C. to 400° C.

25. A process as claimed in claim 1 wherein said temperature is from 250° C. to 300° C.

26. A process for the selective production of methanol comprising contacting a mixture of hydrogen and carbon monoxide with a catalytic amount sufficient to catalyze the reaction of metal substituted lanthanum rhodate having a perovskite structure of the formula $$[La_{1-x}P_x][Rh_{1-y}Q_y]O_3$$

wherein P and Q are each one or more cations whose ionic radii, oxidation state and coordination properties are compatible with a perovskite or distorted perovskite structure and wherein x and y are each from about 0.01 to about 0.99, wherein the hydrogen to carbon monoxide mole ratio is from 20:1 to 1:20 and the reaction is carried out at a pressure of from 100 psig to 15000 psig and a temperature of from 150° C. to 450° C.

27. A process as claimed in claim 26 wherein said cation Q is a metal of Group VIII of the Periodic Table.

28. A process as claimed in claim 27 wherein said Group VIII metal is iron.

29. A process as claimed in claim 27 wherein said Group VIII metal is nickel.

30. A process as claimed in claim 27 wherein said group VIII metal is cobalt.

31. A process as claimed in claim 26 wherein said cation Q is a metal of Group IB of the Periodic Table.

32. A process as claimed in claim 31 wherein said Group IB metal is copper.

33. A process as claimed in claim 26 wherein said cation Q is a metal of Group IIB of the Periodic Table.

34. A process as claimed in claim 33 wherein said Group IIB metal is zinc.

35. A process as claimed in claim 26 wherein said cation Q is a metal of Group IVB of the Periodic Table.

36. A process as claimed in claim 35 wherein said Group IVB metal is titanium.

37. A process as claimed in claim 26 wherein said cation Q is a metal of Group VB of the Periodic Table.

38. A process as claimed in claim 27 wherein said Group VB metal is vanadium.

39. A process as claimed in claim 26 wherein said cation Q is a metal of Group VIB of the Periodic Table.

40. A process as claimed in claim 39 wherein said Group VIB metal is chromium.

41. A process as claimed in claim 26 wherein said cation Q is a metal is Group VIIB of the Periodic Table.

42. A process as claimed in claim 26 wherein said cation P is of Group IIA of the Periodic Table.

43. A process as claimed in claim 42 wherein said Group IIA metal is strontium.

44. A process as claimed in claim 26 wherein said cation P or Q is an actinide.

45. A process as claimed in claim 44 wherein said actinide is thorium.

46. A process as claimed in claim 44 wherein said actinide is uranium.

47. A process as claimed in claim 27 wherein said Group VIII metal is platinum.

48. A process as claimed in claim 26 wherein said metal substituted lanthanum rhodate is substituted with more than one metal.

* * * * *